(12) United States Patent
Goetz et al.

(10) Patent No.: US 6,939,565 B2
(45) Date of Patent: Sep. 6, 2005

(54) **PROTEASE INHIBITORS OF THE COAGULATION CASCADE ISOLATED FROM *DYSIDEA* SPONGES**

(75) Inventors: Gilles H. Goetz, Chesterfield, MO (US); George G. Harrigan, St. Louis, MO (US); John J. Likos, St. Louis, MO (US); Thomas P. Kasten, O'Fallon, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/759,667

(22) Filed: Jan. 16, 2004

(65) Prior Publication Data

US 2004/0147456 A1 Jul. 29, 2004

Related U.S. Application Data

(62) Division of application No. 10/307,803, filed on Dec. 2, 2002, now Pat. No. 6,716,869
(60) Provisional application No. 60/341,527, filed on Dec. 17, 2001.

(51) Int. Cl.$^7$ ...................... A61K 35/56; C07D 209/14
(52) U.S. Cl. ...................... 424/520; 548/468; 424/537
(58) Field of Search .............................. 548/428, 468; 424/537, 520

(56) References Cited

U.S. PATENT DOCUMENTS

| 5,023,236 A | | 6/1991 | Edgington et al. |
| 5,856,309 A | * | 1/1999 | Konetschny-Rapp et al. . 514/18 |
| 5,932,567 A | | 8/1999 | Seitz et al. |
| 6,218,365 B1 | | 4/2001 | Adang et al. |

FOREIGN PATENT DOCUMENTS

| DE | 44 36 772 A1 | 4/1996 |
| WO | WO 96/24609 A1 | 8/1996 |

OTHER PUBLICATIONS

Supplementary Partial European Search Report of US02/40001 dated Dec. 2, 2004.
Bachand et al., "Potent and Selective Bicyclic Lactam Inhibitors of Thrombin. Part 4. Transition State Inhibitors." Bioorg. Med. Chem. Lett, 2001, pp. 287–290, vol. 11.
Claeson, G., "Synthetic Peptides and Peptidomimetics as Substrates and Inhibitors of Thrombin and other Proteases in Blood Coagulation Systems." Blood Coagulation and Fibrinolysis, 1994, pp. 411–436, vol. 5.
Fujii et al., "Comparative Study of Toxic and Non–Toxic Cyanobacterial Products: A Novel Glycoside, Suomilide from Non–toxic Nodularia Spumeigena HKVV." Tetrahedron Lett., 1997, pp. 5529–5532, vol. 38, No. 31.
Handin, R., "Bleeding and Thrombosis." Harrison's Principles of Internal Medicine, 12th Edition, 1991, pp. 348–353, McGraw–Hill, Inc., New York.

Harrigan et al. "Dysideaprolines A–F and Barbaleucamides A–B, Novel Polychlorinates Compounds from a Dysidea Species." J. Nat. Prod., 2001, pp. 1133–1138, vol. 64, No. 9.
Ishida et al., "Aeruginosins, Protease Inhibitors from the Cyanobacterium Microcystis Aeruginosa." Tetrahedron, 1999, pp. 10971–10988, vol. 55, No. 36.
Itou et al., "Oscillapeptins A to F, Serine Protease Inhibitors from the Three Strains of Oscillatoria Agardhil." Tetrahedron, 1999, pp. 6871–6882, vol. 55, No. 22.
Kodani et al., "Aeruginosin 103–A, a Thrombin Inhibitor from the Cyanobacterium Microcystis viridis." J. Nat. Prod., 1998, pp. 1046–1048, vol. 61, No. 8.
Lefkovits et al., "Direct Thrombin Inhibitors in Carbiovascular Medicine." Circulation, 1994, pp. 1522–1536, vol. 90, No. 3.
Majerus, et al., "Anticoagulant, Thrombolytic, and Antiplatlet Drugs." Goodman & Gilman's The Pharmacological Basis of Therapeutics, Ninth Edition, 1996, pp. 1341–1359, McGraw–Hill, New York.
Matsuda et al., "Aeruginosins 102–A and B, New Thrombin Inhibitor from the Cyanobacterium Microcystis Viridis (NIES–102)." Tetrahedron, 1996, pp. 14501–14506, vol. 52, No. 46.
Murakami et al., "Aeruginosin 298–A, A Thrombin and Trypsin Inhibitor From the Blue–Green Alga Microcystis Aeruginosa," Tetrahedron Lett, 1994, pp. 3129–3132. vol. 35, No. 19.
Murakami et al., "Aeruginosin 98–A and B, Trypsin Inhibitors from the Blue–Green Alga Microcystis Aeruginosa." Tetrahedron Lett., 1995, pp. 2785–2788, vol. 36, No. 16.
Radau et al., "Synthesis of a Cyanopeptide–analogue with Trypsin Activating Properties." Bioorg. Med. Chem. Lett., 2000, pp. 779–781, vol. 10.
Raj et al. "Long–term Oral Anticoagulant Therapy: Update on Indications, Therapeutic Ranges, and Monitoring." The American Journal of the Medical Sciences, 1994, pp. 128–132, vol. 307, No. 1.
Sandler et al., "Atomic Structure of the Trypsin–Aeruginosin 98–B Complex." J. Am. Chem. Soc., 1998, pp. 595–596, vol. 120, No. 3.
Shin et al., "Aeruginosins 205A and –B, Serine Protease Inhibitory Glycopeptides from the Cyanobacterium Oscillatoria agardhil (NIES–205)." J. Org. Chem, 1997, pp. 1810–1813, vol. 62, No. 6.

(Continued)

*Primary Examiner*—Joseph K. McKane
*Assistant Examiner*—Janet L. Coppins (57) ABSTRACT

The present invention is directed toward a composition comprising a compound isolated from *Dysidea* species sponges that is capable of inhibiting serine proteases of the coagulation cascade. In particular, this composition inhibits the TF/VIIa complex of the coagulation cascade. The invention is also directed toward methods employing this composition as a part of anticoagulant therapy.

1 Claim, 3 Drawing Sheets

OTHER PUBLICATIONS

Steiner et al., "Structure of Thrombin Inhibited by Aeruginosin 298–A from a Blue–Green Alga." J. Am. Chem. Soc., 1998, pp. 597–598, vol. 120, No. 3.

Tapparelli et al., "Synthetic Low–Molecular Weight Thrombin Inhibitors: Molecular Design and Pharmacological Profile." Trends in Pharmacological Sciences, 1993, pp. 366–376, vol. 14.

Valls et al., "Total Synthesis and Reassignment of Configuration of Aeruginosin 298–A." J. Am. Chem. Soc., 2000, pp. 11248–11249, vol. 122, No. 45.

Weitz et al., "New Anticoagulant Strategies." Laboratory and Clinical Medicine, 1993, pp. 364–373, vol. 122, No. 4.

WIPF et al., "Total Synthesis and Stereochemical Revision of (+)– Aeruginosin 298–A." Org. Lett., 2000, pp. 4213–4216, vol. 2, No. 26.

PCT/US02/40001 PCT International Search Report completed May 25, 2003.

* cited by examiner

———→ gHMBC   - - - - - ROESY

FIGURE 3

PROTEASE INHIBITORS OF THE COAGULATION CASCADE ISOLATED FROM *DYSIDEA* SPONGES

CROSS REFERENCE TO RELATED APPLICATIONS

This is a divisional application and claims priority from U.S. patent application Ser. No. 10/307,803 filed Dec. 2, 2002 now U.S. Pat. No. 6,716,869, which claims priority from provisional application Ser. No. 60/341,527 filed on Dec. 17, 2001, which are hereby incorporated by reference in their entirety.

FIELD OF THE INVENTION

The present invention is directed toward a composition that inhibits certain enzymes of the coagulation cascade. More particularly, the invention relates to a composition comprising a compound isolated from *Dysidea* sponges that may be used for the prevention and treatment of thrombotic conditions such as coronary artery and cerebrovascular disease.

BACKGROUND OF THE INVENTION

Hemorrhage, intravascular thrombosis, and embolism are common clinical manifestations of many diseases [see R. I. Handin in *Harrison's Principles of Internal Medicine* (J. D. Wilson, et al. eds., 12th ed. 1991) New York, McGraw-Hill Book Co., pp. 348–351]. The normal hemostatic system limits blood loss by precisely regulated interactions between components of the vessel wall, circulating blood platelets, and plasma proteins. Unregulated activation of the of the hemostatic system, however, may cause thrombosis, which can reduce blood flow to critical organs like the brain and myocardium. Physiological systems control the fluidity of blood in mammals [see P. W. Majerus, et al. in *Goodman & Gilman's The Pharmacological Basis of Therapeutics* (J. G. Hardman & L. E. Limbird, eds., 9th ed. 1996) New York, McGraw-Hill Book Co., pp. 1341–1343]. Blood must remain fluid within the vascular systems and yet quickly be able to undergo hemostasis. Hemostasis, or clotting, begins when platelets first adhere to macromolecules in subendothelian regions of injured and/or damaged blood vessels. These platelets aggregate to form the primary hemostatic plug and stimulate local activation of plasma coagulation factors leading to generation of a fibrin clot that reinforces the aggregated platelets.

Plasma coagulation factors, also referred to as protease zymogens, include factors II, V, VII, VIII, IX, X, XI, and XII. These coagulation factors or protease zymogens are activated by serine proteases leading to coagulation in a so called "coagulation cascade" or chain reaction. Coagulation or clotting occurs in two ways through different pathways. An intrinsic or contact pathway leads from XII to XIIa to XIa to IXa and to the conversion of X to Xa. Xa with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by Xa. Factor VIIa, a plasma protease, is exposed to, and combines with its essential cofactor tissue factor (TF) which resides constitutively beneath the endothelium. The factor VIIa/TF complex that forms proteolytically activates its substrates, factors IX and X, triggering a cascade of reactions that lead to the generation of thrombin and a fibrin clot as described above. The many different coagulation factors, coupled with the two distinct coagulation pathways, have led researchers to search for compounds that efficaciously and selectively control the clotting process. In addition, these compounds may provide a better understanding of the pathways involved in the coagulation process.

While clotting as a result of an injury to a blood vessel is a critical physiological process for mammals, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

Although direct thrombin inhibitors of various structural classes have been identified recently (Tapparelli et al., *Trends in Pharmacological Sciences* 14: 366–376 (1993); Claeson, *Blood Coagulation and Fibrinolysis* 5: 411–436 (1994); Lefkovits and Topol, *Circulation* 90(3): 1522–1536 (1994), to date only three classes of compounds (heparins, low-molecular weight heparins and coumarins, such as warfarin) have been used in anticoagulant therapy. Each class has severe limitations and liabilities (Weitz and Hirsh, *Journal of Laboratory Clinical Medicine* 122: 364–373 (1993); Raj et al., *The American Journal of the Medical Sciences* 307(2): 128 (1994)). All three classes indirectly inhibit thrombin. Heparin and low-molecular weight heparins augment anti-thrombin III and/or heparin cofactor II inhibition of thrombin, whereas coumarins inhibit vitamin K-dependent post-translational modifications. Close monitoring and titration of therapeutic doses is required when employing these agents due to patient variability. Hemorrhagic complications due to bleeding are an encountered side effect. In fact, bleeding remains as the most common side effect of long term oral anticoagulant therapy. Lack of activity in arterial thrombosis in the case of heparin is due to its inability to inhibit clot bound thrombin. Lack of oral activity in the case of heparins and low-molecular weight heparins preclude their use for chronic administration.

SUMMARY OF THE INVENTION

One aspect of the present invention provides a compound which may be isolated from *Dysidea* sp. sponges that may be beneficially employed in anticoagulant therapy. The compound corresponds to structure (1):

(1)

or a pharmaceutically acceptable salt, prodrug, tautomer or isomer thereof.

In yet another aspect of the present invention is provided a pharmaceutical composition comprising a compound corresponding to structure (1) or a pharmaceutically acceptable salt, prodrug, tautomer or isomer thereof and at least one pharmaceutically acceptable carrier.

In a further aspect of the invention is provided an extract from a *Dysidea* sponge comprising a compound having structure (1) or a pharmaceutically acceptable salt, prodrug, tautomer or isomer thereof.

In still another aspect of the present invention is provided methods for preventing and treating thrombotic conditions, such as coronary artery disease, cerebrovascular disease, and other coagulation related disorders by administering a compound having structure (1) or a pharmaceutically acceptable salt, prodrug, tautomer or isomer thereof to a subject.

Other features and aspects of the present invention will be in part apparent to those skilled in the art and in part pointed out in the detailed description provided below.

BRIEF DESCRIPTION OF THE DRAWINGS

These and other features, aspects, and advantages of the present invention will become better understood with regard to the following description, appended claims and accompanying figures where:

ABBREVIATIONS AND DEFINITIONS

To facilitate understanding of the invention, a number of terms and abbreviations as used herein are defined below:

The term "elimination" is generally meant to encompass any one or more of the following reactions: (1) a reaction that results in a compound fragmenting into two or more compounds; and (2) a reaction that results in one or more groups being removed from a compound without being replaced by other groups.

"Extract" means crude extract, purified extract and purified composition or compounds obtained by purification of the extract.

The term "hydrolysis" is generally meant to encompass any one or more of the following reactions: (1) any reaction which results in the addition of a nucleophile to a compound to form a new bond with concurrent loss of a group from the compound; (2) any reaction which results in the addition of water to a compound; and (3) any reaction that results in the rupture of one or more chemical bonds by reaction with, and involving the addition of, the elements of water.

"IC$_{50}$" means the concentration (in mol L$^{-1}$) that reduces a specified response to 50% of its former value.

The term "inhibitor" when used herein specifically refers to an enzyme inhibitor unless otherwise indicated. Enzyme inhibitors are agents and/or compounds that stop, prevent, or reduce the rate of an enzymatic reaction via any mechanism including, but not limited to, competitive inhibition, non-competitive inhibition, and uncompetitive inhibition.

The term "inhibition" when used herein in phrases such as "serine protease inhibition" means any decrease in enzyme activity as compared to that which would occur in the absence of the compound corresponding to structure 1.

The term "oxidation" is generally meant to encompass any one or more of the following reactions: (1) a reaction that results in an increase in the oxidation number of an atom in a compound, whether the atom is uncharged or charged and whether free or covalently bound; (2) a reaction that results in the loss of hydrogen from a compound; (3) a reaction that results in the loss or removal of one or more electrons from a compound, with or without concomitant loss or removal of a proton or protons; (4) the action or process of reacting a compound with oxygen; and (5) a reaction that results in the addition of one or more oxygen atoms to a compound.

The term "physiological conditions" are those conditions characteristic to an organism's (to a human beings) healthy or normal functioning.

"Purified" means partially purified and or completely purified. Thus, a "purified composition" may be either partially purified or completely purified.

The term "reduction" is generally meant to encompass any one or more of the following reactions: (1) any reaction which results in a decrease in the oxidation number of an atom in a compound; and (2) any reaction that results in oxygen being withdrawn from, hydrogen being added to, or an electron being added to (with or without the addition of a proton) a compound.

"Species" as utilized herein, is a fundamental taxonomic category ranking below a genus and consisting of a group of closely related individuals.

The term "subject" for purposes of treatment or prevention includes any human or animal subject who is susceptible to a thrombolytic condition. The subject can be a domestic livestock species, a farm animal, a laboratory animal species, a zoo animal or a companion animal. In one embodiment, the subject is a mammal. In an alternative of this embodiment, the mammal is a human being.

As used herein, a "surgical procedure" is meant to embrace those procedures that have been classically regarded as surgical procedures as well as interventional cardiology procedures such as arteriography, angiography, angioplasty and stenting.

The term "thrombolytic condition," as used herein unless otherwise indicated, encompasses vaso-occlusive events or related disorders including but not limited to, unstable angina, refractory angina, atrial fibrillation, thrombotic stroke, embolic stroke, deep vein thrombosis, disseminated intravascular coagulation, ocular build up of fibrin, and reocclusion or restenosis of recanalized vessels myocardial infarction, stroke, transient ischemic attacks including myocardial infarction and stroke, amaurosis fugax, aortic stenosis, cardiac stenosis, coronary stenosis and pulmonary stenosis. Stenosis is the narrowing or stricture of a duct or canal. Coronary stenosis is the narrowing or stricture of a coronary artery. Cardiac stenosis is a narrowing or diminution of any heart passage or cavity. Pulmonary stenosis is the narrowing of the opening between the pulmonary artery and the right ventricle. Aortic stenosis is narrowing of the aortic orifice of the heart or of the aorta itself.

As used herein, the "treatment" of a subject is intended to embrace both prophylactic and therapeutic treatment, and can be used either to limit or to eliminate altogether the symptoms or the occurrence of a thrombolytic condition.

DETAILED DESCRIPTION OF THE PREFERRED EMBODIMENT

It has been discovered that a composition isolated and purified from marine *Dysidea* species sponges inhibits the TF/VIIa complex and other serine proteases of the coagulation cascade. In one aspect of the invention, the composition comprises a compound corresponding to structure (1):

(1)

In another aspect of the invention, the composition may include a tautomeric, geometric or stereoisomeric form of a compound having structure (1). The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans").

In yet another aspect of the invention, the composition may include a prodrug of the compound having formula (1). Any prodrug moiety commonly known in the art may be added to any suitable substituent of the compound having formula (1). Generally speaking, the prodrug can be converted under physiological conditions to the biologically active drug by a number of chemical and biological mechanisms. In one embodiment, conversion of the prodrug to the biologically active drug can be accomplished by hydrolysis of the prodrug moiety provided the prodrug moiety is chemically or enzymatically hydrolyzable with water. The reaction with water typically results in removal of the prodrug moiety and liberation of the biologically active drug. Yet another aspect of the invention provides conversion of the prodrug to the biologically active drug by reduction of the prodrug moiety. Typically in this embodiment the prodrug moiety is reducible under physiological conditions in the presence of a reducing enzymatic process. The reduction preferably results in removal of the prodrug moiety and liberation of the biologically active drug. In another embodiment, conversion of the prodrug to the biologically active drug can also be accomplished by oxidation of the prodrug moiety. Typically in this embodiment, the prodrug moiety is oxidizable under physiological conditions in the presence of an oxidative enzymatic process. The oxidation preferably results in removal of the prodrug moiety and liberation of the biologically active drug. A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Of course, any prodrug compound of the present invention may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

Yet another aspect of the invention provides organic extracts comprising a compound corresponding to structure 1 or an isomer or tautomer thereof isolated and purified from marine *Dysidea* species sponges, irrespective of the degree of purification. The extraction process may be performed as detailed herein or in accordance with any procedure known in the art.

Indications to be Treated or Prevented

In one aspect of the present invention, the composition may be employed to treat or prevent a thrombolytic condition.

In yet another aspect of the invention, the composition may be employed in a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs.

In still another aspect of the invention, the composition may also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

In yet another embodiment, the composition may be used to study the mechanism of action of coagulation cascade serine proteases to enable the design of better inhibitors and development of better assay methods.

In addition to the composition of the invention, another agent may also be included, which when administered as part of a combination therapy with the composition of the invention, provides enhanced treatment options as compared to administration of either agent alone for the particular thrombolytic condition indication being treated. The agent administered with the composition of the invention is referred to herein as a "thrombolytic agent." Generally speaking, suitable thrombolytic agents include anti-platelet agents, anticoagulation agents, and cardiovascular therapeutic agents.

In one embodiment, when general thrombolytic conditions are being treated, the thrombolytic agent may belong to a class of compounds that cause a reduction in platelet aggregation and thereby diminishes the size of or prevents the formation of a thrombus or occlusion. One such class of compounds is anti-platelet inhibitors that ameliorate prostaglandin synthesis. These agents include salicylates (e.g. aspirin) and other NSAIDS, ticlopidine, or clopidrogel. In a further embodiment, the anti-platelet inhibitor is a GP IIb/IIIa inhibitor.

In yet another embodiment, when indications such as unstable angina, thrombolytic occlusions or prevention of reocculsion after angioplasty and restenosis are being treated, the thrombolytic agent co-administered along with the composition of the invention include fibrinogen receptor antagonists, anti-coagulants such as warfarin or heparins, and plasminogen activators, such as tissue plasminogen activator (tPA) or streptokinase. In still another embodiment, when the indication being treated is coronary artery disease or patients subjected to angioplasty procedures, suitable agents include antihypercholesterolemics (e.g. HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (e.g. loop diuretics, thiazide type diuretics, nitrates, aldosterone antagonistics (e.g. spironolactone and epoxymexlerenone), angiotensin converting enzyme (e.g. ACE) inhibitors, angiotensin II receptor antagonists, beta-blockers, antiarrythmics, antihypertension agents, and calcium channel blockers to treat or prevent atheriosclerosis.

The timing of the administration of the composition comprising a compound having formula (1) in relation to the administration of the thrombolytic agent may also vary from subject to subject and depend upon the thrombolytic condition being treated. In one embodiment of the invention, the composition and thrombolytic agent may be administered substantially simultaneously, meaning that both agents may be administered to the subject at approximately the same time. For example, the composition may be administered during a continuous period beginning on the same day as the beginning of the thrombolytic agent and extending to a period after the end of the thrombolytic agent. Alternatively, the composition comprising a compound of formula (1) and thrombolytic agent may be administered sequentially, meaning that they are administered at separate times during separate treatments. In one embodiment, for example, the composition may be administered during a continuous period beginning prior to administration of the thrombolytic agent and ending after administration of the thrombolytic agent. Of course, it is also possible that the composition comprising a compound of formula (1) may be administered either more or less frequently than the thrombolytic agent. One skilled in the art can readily design suitable treatment regiments for a particular subject depending on the particular thrombolytic condition being treated. Moreover, it will be apparent to those skilled in the art that it is possible, and perhaps desirable, to combine various times and methods of administration in the practice of the present invention.

In some aspects, the invention provides treatment for subjects who are at risk of a thrombolytic condition. These subjects may or may not have had a previous thrombolytic condition. The invention embraces the treatment of subjects prior to a thrombolytic condition, at a time of a thrombolytic condition and following a thrombolytic condition. In one embodiment, the subject may exhibit symptoms of a thrombolytic condition.

The invention also embraces the treatment of a subject that has an abnormally elevated risk of a thrombolytic condition. The subject may have vascular disease. The vascular disease may be selected from the group consisting of arteriosclerosis, cardiovascular disease, cerebrovascular disease, renovascular disease, mesenteric vascular disease, pulmonary vascular disease, ocular vascular disease or peripheral vascular disease.

In one embodiment, however, the subject has had a primary thrombolytic condition. The composition of the invention may be administered to a subject following such a primary thrombolytic condition. The method of the invention also embraces treatment of a subject to reduce the risk of a secondary thrombotic event or to inhibit the propagation of an existing thrombotic event. By way of example, the thrombotic event may be selected from the group consisting of arterial thrombosis, coronary thrombosis, heart valve thrombosis, coronary stenosis, stent thrombosis and graft thrombosis. The thrombolytic condition also includes disorders or conditions that may arise from a thrombotic event or a thromboembolic event and in this regard a thrombolytic condition includes, but is not limited to myocardial infarction, stroke and transient ischemic attack. In one embodiment, the thrombolytic condition is myocardial infarction. In yet another embodiment, the subject has had a myocardial infarction. A subject who has hypercholesterolemia, hypertension or atherosclerosis also can be treated by the methods of the invention.

In yet another embodiment, the subject is one who will undergo an elective surgical procedure. The composition of the invention may be administered to such a subject prior to the elective surgical procedure. The method of the invention can also be directed towards a subject who has undergone a surgical procedure. The surgical procedure, whether elective or not, can be selected from the group consisting of coronary angiography, coronary stent placement, coronary by-pass surgery, carotid artery procedure, peripheral stent placement, vascular grafting, thrombectomy, peripheral vascular surgery, vascular surgery, organ transplant, artificial heart transplant, vascular angioplasty, vascular laser therapy, vascular replacement, prosthetic valve replacement and vascular stenting.

Formulations, Routes of Administration and Dosages

A further aspect of the invention encompasses a pharmaceutical composition comprising the compound having structure (1) as a pharmaceutically-acceptable salt. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of the compound may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts the compound include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compound by reacting, for example, the appropriate acid or base with the compound of the present invention.

The present invention also comprises a pharmaceutical composition comprising a therapeutically-effective amount of the compound in association with at least one pharmaceutically-acceptable carrier, adjuvant or diluent. Pharmaceutical compositions of the present invention can comprise the active compound in association with one or more non-toxic, pharmaceutically-acceptable carriers and/or diluents and/or adjuvants (collectively referred to herein as "carrier" materials) and, if desired, other active ingredients.

The active compound of the present invention may be administered by any suitable route, preferably in the form of a pharmaceutical composition adapted to such a route, and in a dose effective for the treatment intended. Generally speaking, the active compound or composition may, for example, be administered orally, intravascularly, intraperitoneally, subcutaneously, intramuscularly, oculary, or topically. For treating ocular build up of fibrin, the compound may be administered intraocularly or topically as well as orally or parenterally.

In one embodiment, the composition can be administered in the form of an injection or implant preparation that may be formulated in such a manner as to permit a sustained release of the active ingredient. The active ingredient can be compressed into pellets or small cylinders and implanted subcutaneously or intramuscular as depot injections or implants. Implants may employ inert materials such as biodegradable polymers or synthetic silicones, for example, Silastic, silicone rubber or other silicon containing polymers.

The composition can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In yet another embodiment, the composition may be delivered by the use of monoclonal antibodies as individual carriers to which the compound molecules are coupled. The composition may also be coupled with soluble polymers as targetable drug carriers. Such polymers can include polyvinylpyrrolidone, pyran copolymer, polyhydroxypropyl-methacrylamide-phenol, polyhydroxyethyl-aspartamide-phenol, or ployethyleneoxide-polylysine substituted with palmitoyl residues. Furthermore, the composition may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound to be administered and the dosage regimen for treating a disease condition with the compound and/or composition of this invention depends on a variety of factors, including the age, weight, sex and medical condition of the subject, the severity of the disease, the route and frequency of administration, and the particular compound employed, and thus may vary widely.

The pharmaceutical composition may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The composition may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The composition can also be administered by a transdermal device. Typically, topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner. While the phase may comprise merely an emulsifier, it may comprise a mixture of at least one emulsifier with a fat or an oil or with both a fat and an oil. Typically, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compound of the present invention are ordinarily combined with one or more adjuvants appropriate to the indicated route of administration. If administered per os, the compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compound may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Organic Extraction from Dysidea

In one aspect of the invention, the composition comprising a compound corresponding to structure 1 may be isolated and purified from marine *Dysidea* species sponges. The *Dysidea* species biological material may be obtained from Scripps Oceanographic Institute, La Jolla, Calif. (NCI 815 and NCI 1517) or any other source.

In order to prepare the organic extract, a Dysidea species sponge sample may be ground into a fine powder, the resultant powder is extracted with a solvent, and the extraction solvent is removed from the extract. If desired, the resultant extract may be further purified to yield a purified extract or one or more purified compositions. The grinding step may be accomplished by any commonly known method for grinding a sponge substance. For example, the sponge may be passed through a grinder to obtain a fine powder.

After the sponge has been ground into a fine powder, it may then be combined with an extraction solvent. The solution is then stirred at a temperature, and for a period of time, which is effective to obtain an extract with the desired inhibitory effects on the protease target. The solution is typically not overheated, as this may result in degradation and/or denaturation of compounds in the extract. The solution may be stirred at a temperature between about room temperature (25° C.) and the boiling point of the extraction solvent. Generally speaking, the solution is stirred at about room temperature.

The length of time that the sponge is exposed to the extraction solvent is not critical. Up to a point, the longer it is exposed to the extraction solvent, the greater is the amount of extract that may be recovered. Typically, the solution is stirred for at least 1 minute, more typically, for at least 15 minutes, and most typically, for at least 60 minutes.

The extraction process is desirably carried out using an organic solvent or a mixture of organic solvents. Organic solvents which may be used in the extraction process, include but are not limited to hydrocarbon solvents, ether solvents, chlorinated solvents, acetone, ethyl acetate, butanol, ethanol, methanol, isopropyl alcohol and mixtures thereof. Hydrocarbon solvents which may be used in the present invention include heptane, hexane and pentane. Ether solvents which may be used in the present invention include diethyl ether. Chlorinated solvents which may be used in the present invention include dichloromethane and chloroform. Generally speaking, the solvent utilized for such extraction is a nonpolar organic solvent, such as dichloromethane or hexane.

The relative amount of solvent used in the extraction process may vary considerably, depending upon the particular solvent employed. Typically, for each 100 grams of sponge material to be extracted, about 500 mL of extraction solvent would be used. The organic solvent may be removed from the extract by any method known in the field of chemistry for removing organic solvents from a desired product, including, for example, rotary evaporation.

Particular compounds present in the extract may be isolated and purified by those of ordinary skill in the art employing a variety of methods. By way of example, these methods may include column chromatography and fractional distillation. By way of further example, the compound corresponding to structure (1) was purified from the extract by the methods detailed in the Examples below.

Although this invention has been described with respect to specific embodiments, the details of these embodiments are not to be construed as limitations. The following examples are provided to illustrate the present invention and are not intended to limit the scope thereof. Without further elaboration, it is believed that one skilled in the art can, using the preceding description, utilize the present invention to its fullest extent. The following preferred specific embodiments are, therefore, to be construed merely as illustrative, and not limitative of the remainder of the disclosure in any way whatsoever. Those skilled in the art will readily understand that known variations of the conditions and processes of the following preparative procedures can be used to prepare these compounds.

EXAMPLES

Example 1

Isolation of the Compound Corresponding to Structure 1

*Dysidea* species biological material was obtained from Scripps Oceanographic Institute, La Jolla, Calif. (NCI 815 and NCI 1517) and was subjected to the extraction process detailed herein. The liquid sample resulting from the extraction process was subjected to reverse-phase vacuum liquid column chromatography and bioassay-guided semi-preparative reversed-phase HPLC.

Example 2

Determination of Structure

Figure 1:
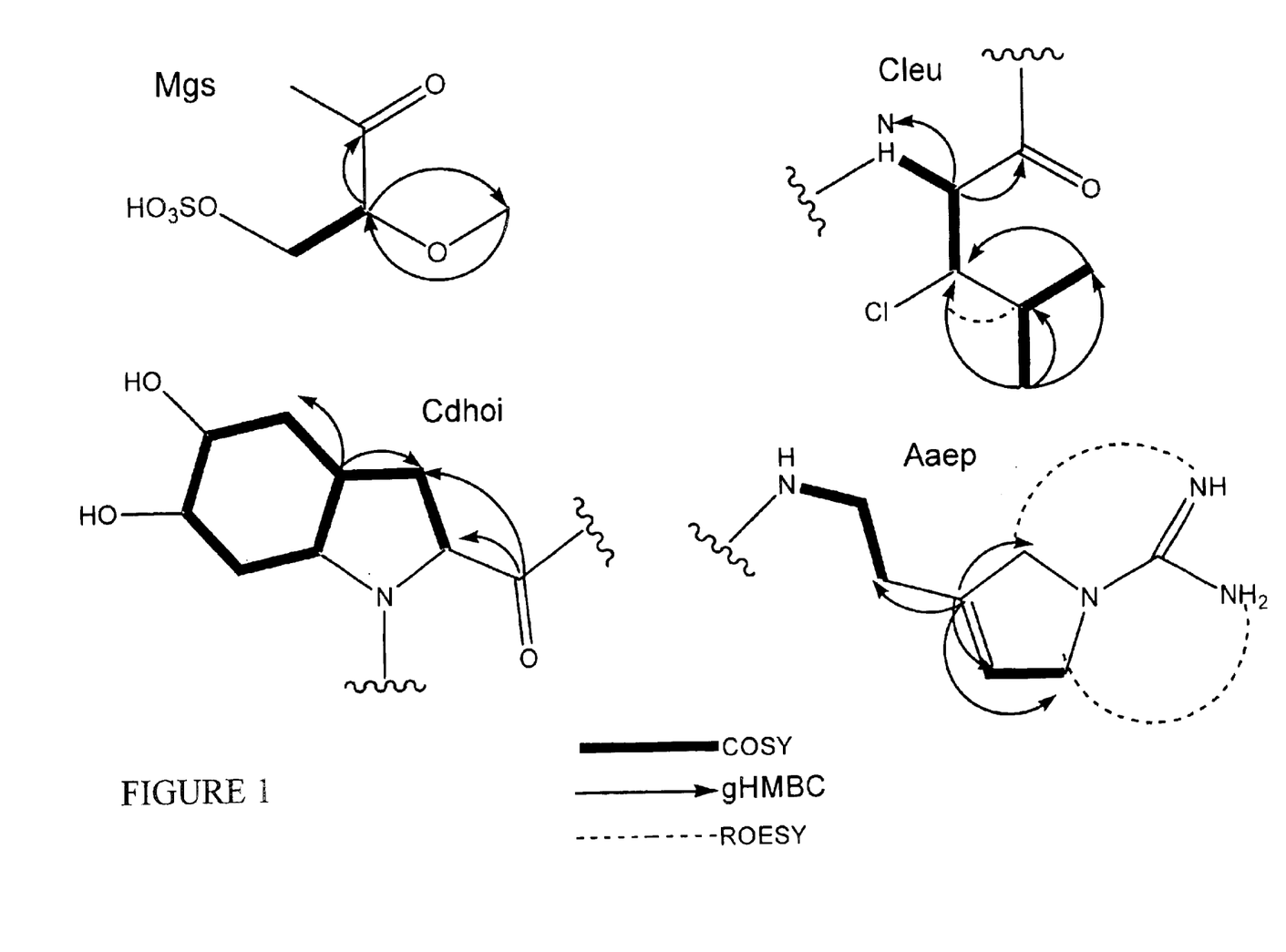
FIG. 1 depicts partial structures of the compound having structure (1) derived from 2D NMR experiments.

The molecular formula was determined to be $C_{26}H_{43}N_6O_{10}ClS$ by HREI-MS and $^{13}C$ NMR data. The presence of chloride was supported by 3:1 isotope ion peaks at m/z 587/589 and 667/669 in the positive EI-MS. The $^1H$ and $^{13}C$ NMR spectra of 1 (Table 1) were suggestive of a peptide. The $^{13}C$ NMR spectrum contained 26 signals, including 3 methyl, 8 methylene, 10 methine, and five non protonated carbons (of which three were carbonyl carbons). Extensive 2D NMR spectra employing $^1H$-$^1H$ COSY, TOCSY, ROESY, gradient and selective HSQC and HMBC experiments led to four partial structures (FIG. 1). These structures were Cleu (3-Chloroleucine), Mgs (2-O-methylglyceric acid 3-O-sulfate), cdhoi (2-carboxy-5,6-dihydroxyoctahydroindole), and Aaep (1-amidino-3-(2-aminoethyl)-3-pyrroline).

Mgs. The connectivity for 2-O-methylglyceric acid 3-O-sulfate was readily determined in a straightforward manner. The H-2 proton at $\delta_H$ 3.87 showed a correlation to the carbonyl carbon at $\delta_C$ 168.9 in the HMBC spectrum, and to H-3a, H-3b in the COSY spectrum. The chemical shifts of C-2 ($\delta_H$ 3.87, $\delta_C$ 80.5) and C-3 ($\delta_H$ 3.94, 3.76, $\delta_C$ 65.7) indicated that both carbons were adjacent to oxygen atoms. In the positive FAB-MS, the fragment ion peak at m/z 587 (M−sulfate+H)$^+$ indicated the presence of sulfate. The correlation between C-2 and the methyl protons at $\delta_H$ 3.26 observed in the HMBC spectrum inferred the position of the methoxy group.

Cleu. The 3-chloroleucine unit was assigned from the COSY and HMBC spectra. The COSY experiment gave straightforward connectivities from amide proton at $\delta_H$ 7.77 to H-2 and H-3, and from methine H-4 at $\delta_H$ 2.15 to H-5 and H-5' methyl protons at $\delta_H$ 0.90 and 0.95, respectively. Connectivity between H-3 and H-4 was established on the basis of a ROESY correlation, confirmed by HMBC cross peaks between H-3 and C-4, C-5 and C-5'.

Aaep. The $^{13}C$ and $^1H$ data of Aaep were consistent with that reported for the Aaep group in suomilide. The connectivities from the C-7 amide proton at $\delta_H$ 7.55 to the C-2 and C-5 pyrroline methylenes ($\delta_H$ 4.09–4.11) were inferred from the COSY and HMBC experiments. Selective HMBC experiments failed to reveal correlations between H-2 and H-5 of 1-amidino-3-(2-aminoethyl)-3-pyrroline and the guanidine group at $\delta_C$ 154.1. No correlation were observed between corresponding carbons and protons in Aaep of suomilide: rather, the connectivity was deduced on the basis of MS/MS experiments.

Figure 3:
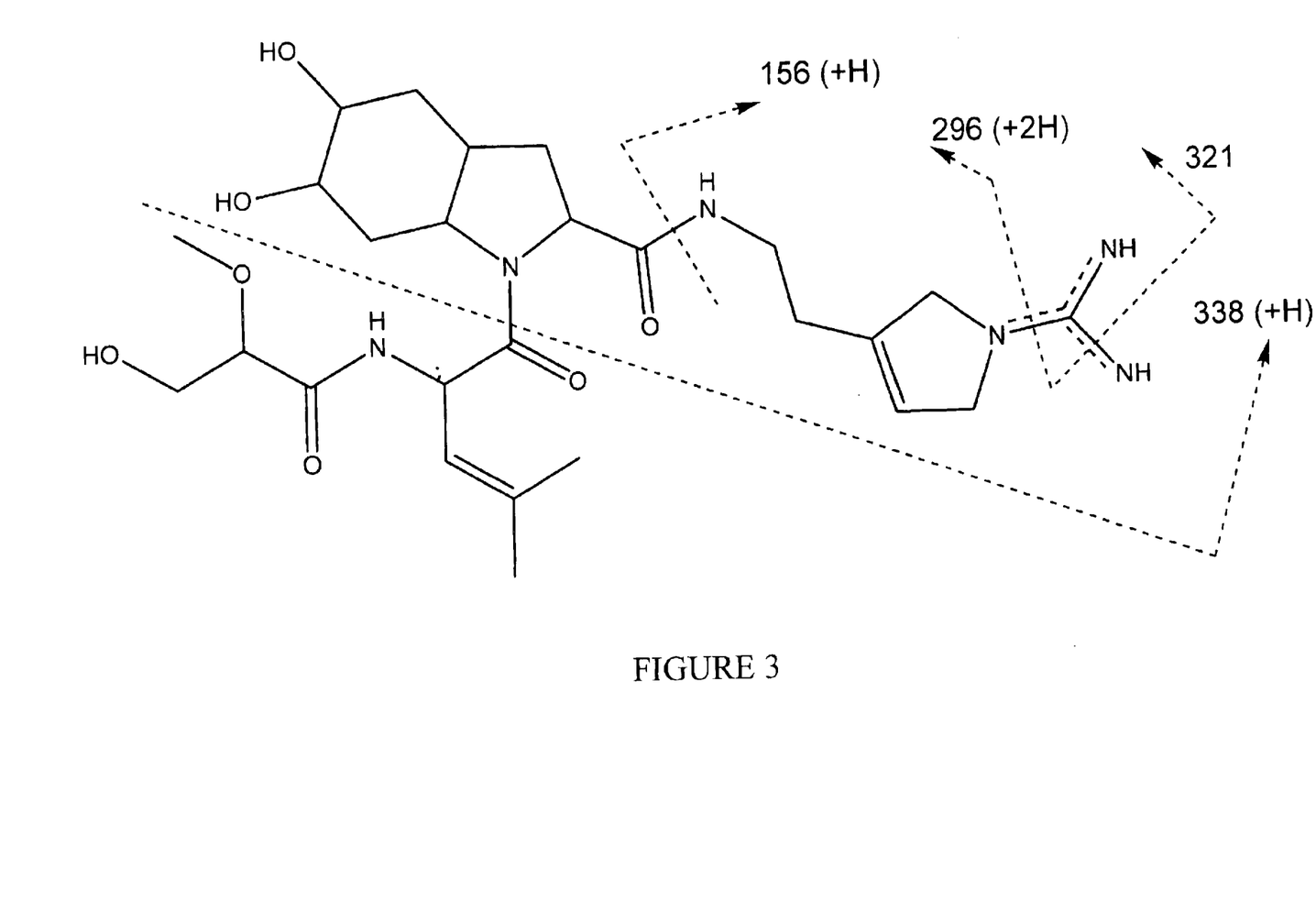
FIG. 3 depicts product ions for [M–SO$_3$–Cl+H]$^+$ at m/z 551 for the compound corresponding to structure (1).

Cdhoi. In the HMBC spectrum H-2 was correlated to the carbonyl carbon at $\delta_C$ 170.9. In the COSY spectrum, the connectivities from H-2 to H-7' were readily determined in a straightforward manner. The chemical shifts of C-2 ($\delta_H$ 4.06, $\delta_C$ 59.8) and C-7' ($\delta_H$ 4.29, $\delta_C$ 54.6) indicated that both carbons were adjacent to the nitrogen atom. In addition to $^{13}C$ chemical shift, COSY correlations between the 2 exchangeable protons at $\delta_H$ 4.76 and $\delta_H$ 4.65, and H-6 and H-5 respectively, supported the located of two hydroxyl groups at C-5 and C-6. In the positive FAB-MS, the fragment ion peak at m/z 338 (M−Cleu−Mgs.+2H)$^+$, along with associated fragment ions, confirmed the absence of chlorine on the Cdhoi ring system (FIG. 3). These data fully supported the presence of the Cdhoi residue.

Figure 2:
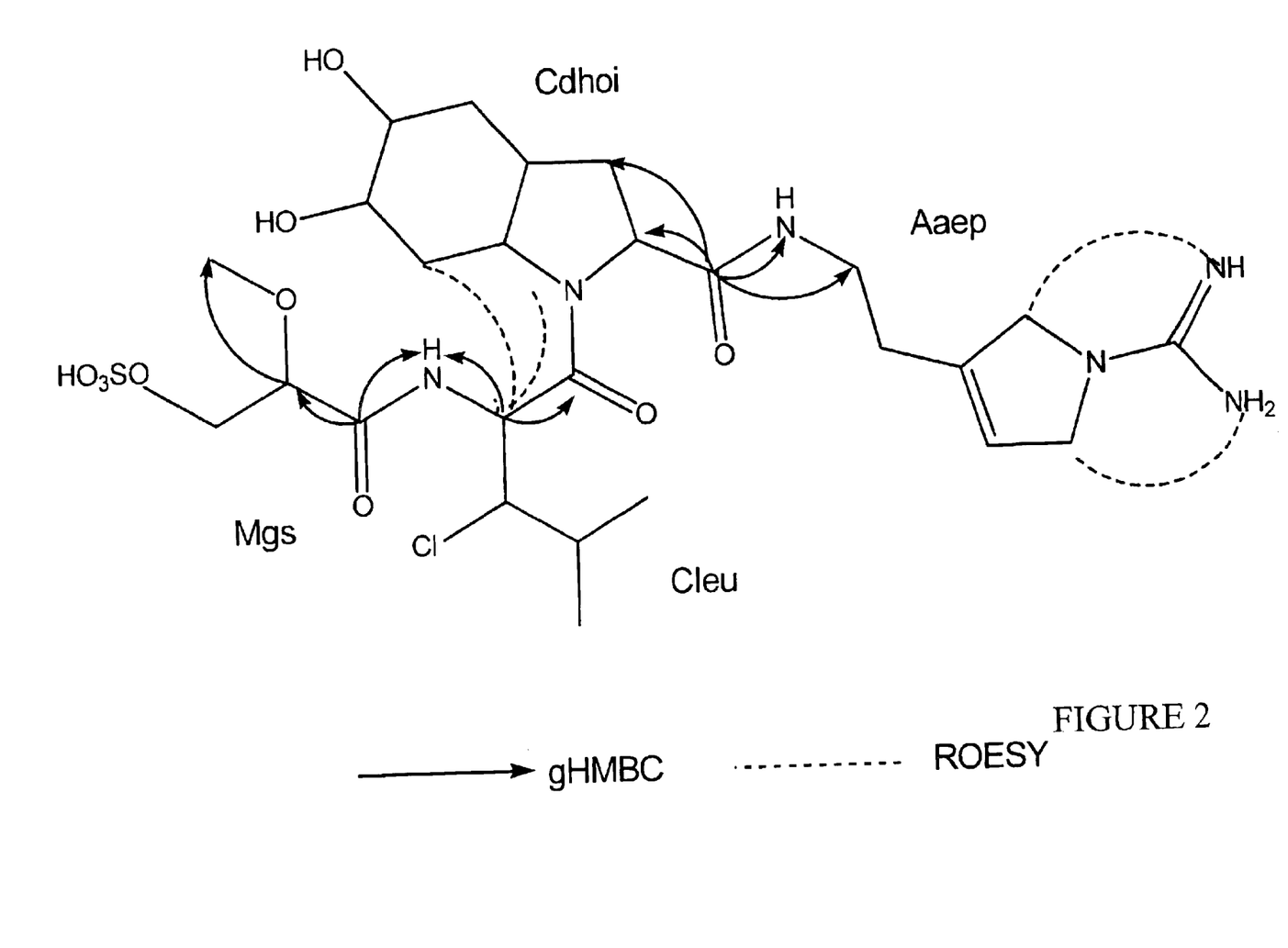
FIG. 2 depicts HMBC and ROSEY correlations for the compound having structure (1).

Assembly of the Partial Structures. The HMBC (Table 1) and ROESY data (FIG. 2) allowed the connection of the partial structures into structure 1. HMBC cross peaks between the NH protons and the carbonyl carbons of the adjacent amino acids, Cleu NH/Mgs CO and Aaep 7-NH/Cdhoi CO, established the partial sequences Mgs-Cleu and Cdhoi-Aaep. The positive FAB-MS fragmentation pattern supported the Cdhoi-Aaep sequence (FIG. 3). The connectivity between Hleu and Ccoi was determined by the ROESY correlation between Cleu H-2 and Cdhoi H-7' and H-4, though no HMBC correlation was observed between these residues.

TABLE 1

$^{13}C$ and $^1H$ NMR data for Structure (1) in DMSO-$d_6$

| Unit | | $^{13}C$ (mult)$^a$ | $^1H$ (mult J Hz) | COSY | ROESY | HMBC$^b$ |
|---|---|---|---|---|---|---|
| Mgs | 1 | 168.9 (s) | | | | 2, 3a, 3b, Hleu: 1-NH |
| | 2 | 80.6 (d) | 3.87 (dd 2.6, 6.2) | 3a | O—Me, Cleu: 1-NH | 3a, OMe |
| | 3a | 65.9 (t) | 3.78 (dd 10.8, 6.2) | 2, 3b | 3b | 2 |
| | 3b | | 3.93 (dd 10.8, 2.6) | 3a | 3a, Cleu: 3 | |
| | O—Me | 57.1 (q) | 3.26 (s) | | 2 | 2 |
| Cleu | 1 | 167.8 (q) | | | | 2, 3 |
| | 2 | 51.9 (d) | 4.87 (dd 10.2, 9.1) | 1-NH, 3 | 1-NH, 3, 5, Cdhoi: 7, 7' | 1-NH, 3 |
| | 3 | 68.52 (d) | 4.11 (m) | 2 | 1-NH, 2, 4, 5, Mgs: 3b | 2, 5, 5' |
| | 4 | 27.9 (d) | 2.17 (m) | 5, 5' | 1-NH, 3, 5, 5' | 2, 3, 5. 5' |
| | 5 | 15.0 (q) | 0.90 (d 6.5) | 4 | 2, 4 | 4, 3, 5' |
| | 5' | 20.6 (q) | 0.95 (d 6.4) | 4 | 3, 4 | 4, 3, 5 |
| | 1-NH | | 7.77 (d 8.7) | 2 | 2, 3, 4, Mgs: 2 | |
| Cdhoi | 1 | 170.9 (q) | | | | 2, 3b, Aaep: 4a, 4b, 7-NH |
| | 2 | 59.8 (d) | 4.06 (m) | 3a, 3b | 3a, Aaep: 7-NH | 3b |
| | 3a | 33.4 (t) | 2.04 (m 6.5) | 2, 3b | 2, 3b | 2 |
| | 3b | | 2.35 (m 6.5) | 2, 3a | 3a, 4b | |
| | 3' | 35.2 (d) | 2.07 (m 6.2) | 4a, 7' | 4b, 7' | 3b, 7 |
| | 4a | 26.6 (t) | 1.91 (m) | 3', 4b | 5 | 3b |
| | 4b | | 1.55 (d 15.1) | 5, 4a | 3b, 3', 5, 7 | |
| | 5 | 67.1 (d) | 3.55 (s broad) | 4b, 6, 5-OH | 4a, 4b, 6 | |
| | 6 | 68.48 (d) | 3.66 (s broad) | 5, 7, 6-OH | 5, 7 | |
| | 7 | 27.6 (t) | 1.93 (2H m) | 4b, 7' | 4b, 6, 7', Cleu: 2 | 3' |

TABLE 1-continued $^{13}C$ and $^1H$ NMR data for Structure (1) in DMSO-$d_6$

| Unit | | $^{13}C$ (mult)[a] | $^1H$ (mult J Hz) | COSY | ROESY | HMBC[b] |
|---|---|---|---|---|---|---|
| | 7' | 54.6 (d) | 4.29 (m 5.8) | 3', 7 | 3', 7, Cleu: 2 | |
| | 5-OH | | 4.65 (d 2.6) | 5 | | |
| | 6-OH | | 4.76 (d 2.6) | 6 | | |
| Aaep | 2 | 55.3 (t) | 4.10 (2H m) | 4 | 4, 6, Gua: NH | |
| | 3 | 136.0 (q) | | | | 2, 4, 5, 6, 7a, 7b |
| | 4 | 119.3 (d) | 5.61 (s) | 2, 5 | 2, 5, 6 | 2, 5, 6 |
| | 5 | 54.1 (t) | 4.11 (2H m) | 4 | 4, 6, Gua: NH | |
| | 6 | 28.4 (t) | 2.24 (2H m 6.5) | 7a, 7b | 2, 4, 5, 7a | 4, 7b |
| | 7a | 36.3 (t) | 3.06 (m) | 6, 7b, 7-NH | 6, 7b, 7-NH | 6, 7-NH |
| | 7b | | 3.26 (m) | 6, 7a, 7-NH | 7a | |
| | 7-NH | | 7.55 (dd t like 5.8) | 7a, 7b | 7a, Cdhoi: 2 | |
| | guanidine | 154.1 (q) | 7.13 (s broad) | | 2, 5 | |

[a]Multiplicity deduced from an APT experiment.
[b]Correlations from H to the indicated C

Example 3

High Throuput Factor VIIa/TF Inbitory Assay

To determine inhibitory activity, the compound having structure (1) was combined with recombinant human factor VIIa in black clear bottom well plates followed by a 10 minute room temperature incubation. Recombinant soluble tissue factor was then added followed by a 15 minute room temperature incubation. Finally, chromozymen tPA substrate was added and the plates were immediately read at 405 nm to determine background absorbance. After incubation, the rate of hydrolysis of the substrate was measured by monitoring the reaction at 405 nm for the release of p-nitroaniline. Percent inhibition of TF/VIIa activity was calculated from OD 405 nm value from the experimental and control sample. All hits 50% of control and less were confirmed and requested for $IC_{50}$ values.

Example 4

HPLC-PDA-MS-Bioassay

An aliquot of sample was injected onto $C_{18}$ reversed-phase column with flow rate of 1 mL/min. Mass spectra were recorded from 150 to 1000 amu in both positive and negative modes using electrospray ionization. A splitter was attached immediately after the HPLC column so that a fraction of the eluent was directed towards the electrospray source. The remaining fraction was collected in deep-well plates. The plates were dried overnight and biassayed. The bioassays yielded the following results:

| $IC_{50}$ Data for VII and Other Factors | |
|---|---|
| VIIa | 9 nM |
| Thrombin | 4 nM |
| Xa | 200 nM |
| Trypsin | 37 nM |

What is claimed is:
1. An extract of a *Dysidea* sponge comprising a compound having the structure:

or a pharmaceutically acceptable salt, prodrug, tautomer or stereoisomer thereof.

* * * * *